(12) United States Patent
Krakovsky

(10) Patent No.: US 7,584,757 B2
(45) Date of Patent: Sep. 8, 2009

(54) PHALLOPLASTY TECHNIQUE

(76) Inventor: Alexander Krakovsky, 7946 Ivanhoe Ave., Suite 106, La Jolla, CA (US) 92037-4516

( * ) Notice: Subject to any disclaimer, the term of this patent is extended or adjusted under 35 U.S.C. 154(b) by 46 days.

(21) Appl. No.: 11/893,947

(22) Filed: Aug. 17, 2007

(65) Prior Publication Data

US 2008/0045784 A1  Feb. 21, 2008

Related U.S. Application Data

(60) Provisional application No. 60/838,695, filed on Aug. 18, 2006.

(51) Int. Cl.
*A61B 19/00* (2006.01)
*A61F 5/00* (2006.01)

(52) U.S. Cl. ......................... 128/898; 600/38

(58) Field of Classification Search ............ 600/38–41; 128/897, 898
See application file for complete search history.

(56) References Cited

U.S. PATENT DOCUMENTS 5,842,969 A * 12/1998 Vikhrev ................. 600/38
5,921,246 A * 7/1999 Cho ..................... 128/898
6,173,714 B1 * 1/2001 Cho ..................... 128/898
6,582,356 B2 * 6/2003 Kim ..................... 600/40
7,273,449 B2 * 9/2007 Moore ................... 600/38

* cited by examiner

*Primary Examiner*—Samuel G Gilbert
(74) *Attorney, Agent, or Firm*—John Ross; John R. Ross, III

(57) ABSTRACT

A technique for penile enlargement. The apparent length of the penis is first increased by cutting ligaments that attach the penis to the pubic bone. Then the girth of the penis is increased by making two cuts making two apertures in the penile skin near the base of the penis and near the glans of the penis and inverting the skin from the top side of the penis so that the glans of the penis protrudes through one of the skin aperture substantially all of the exposed penis protrudes through the other skin aperture, leaving at least the top half of the penis skinless defining a bare penile region. One or more layers of donated skin are attached to the patient's skin covering the bare region. Then the patients skin from the back of his penis is re-inverted approximately back to its original position and covering the donated skin stitched to the patient's skin. The two incisions are then closed.

9 Claims, 4 Drawing Sheets

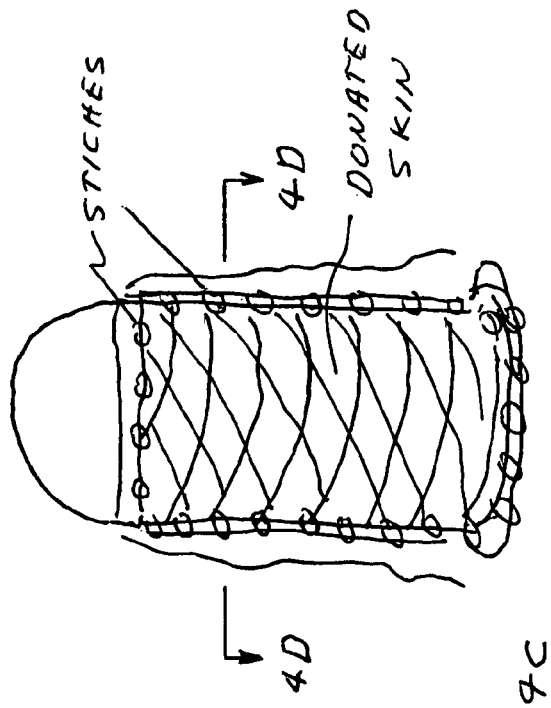
FIG. 4D
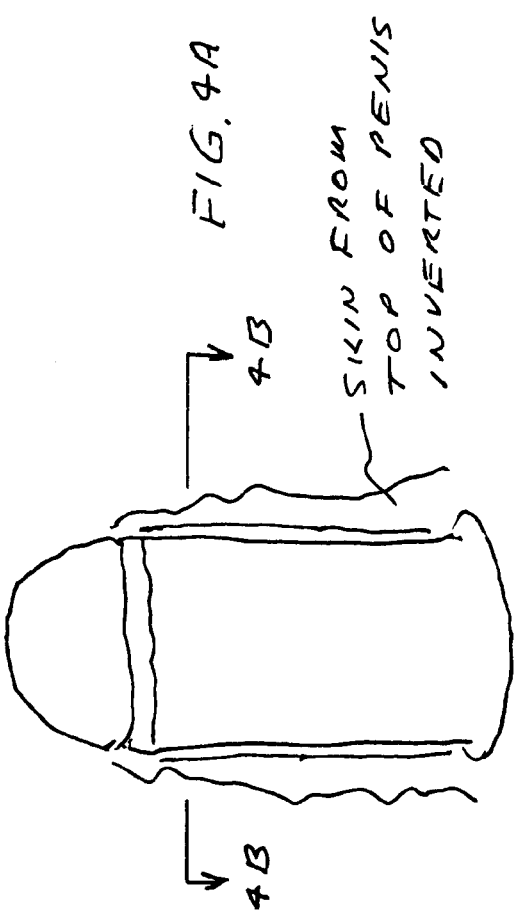
FIG. 4C
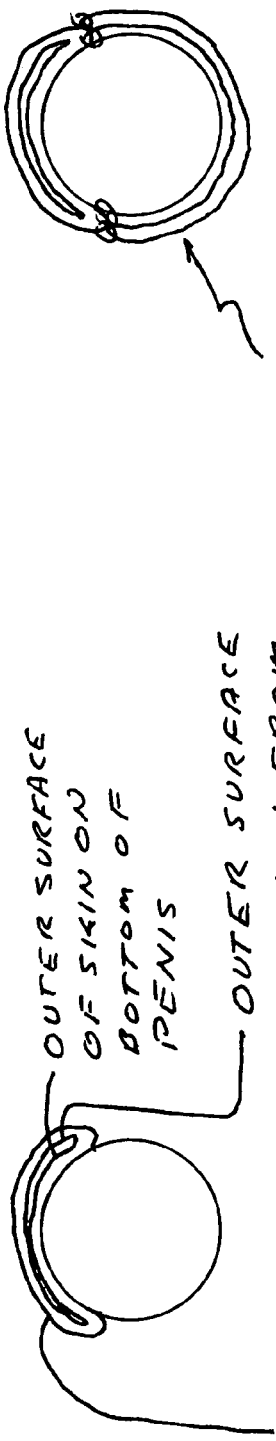
FIG. 4B
FIG. 4A

PHALLOPLASTY TECHNIQUE

CROSS REFERENCE TO RELATED APPLICATIONS

This application claims the benefit of Provisional Application Ser. No. 60/838,695 filed Aug. 18, 2006.

BACKGROUND OF THE INVENTION

Sex Problems

Physiologically, historically, socially and sexually, man's self-esteem and self-image has always been connected to the size of his penis. This can be easily observed in the most ancient artistic pictures and sculptures. From the beginning of our civilization, the human body has been an object of scientific, cultural, spiritual and aesthetic investigations. Ancient Egypt, both Pharaonic and Greco-Roman, has yielded much representational and artistic evidence for the nude human body. In Freud's psychosexual stages of human development, he centered on the sexual pleasure drive and immature (small) penis that he considered as the libidinal object of infantile sexuality in men. Many men are proud or ashamed of their penis-size, shape and performance. There is often anxiety about men's self-confidence due to the size of his penis and functionality. This directly relates to sexual performance, female satisfaction, intimacy and love.

Until recently, men had to accept whatever Mother Nature had given to them. Nowadays, penile enhancement is a process that is available in the plastic and cosmetic surgery fields. Although this subject was taboo some years ago, today many men are interested in learning about how phalloplasty may improve their self-confidence, sexual relationships, female satisfaction, pleasure, intimacy and love. Phalloplasty includes penile lengthening, girth enhancement and glanular enhancement. Phalloplasty is available today and may improve the man's relationships, sexuality, intimacy and love.

Anatomy and Physiology

The report on study conducted in Kent, England, in the seventies by a group of doctors, established a procedure for penis lengthening enlargement. Sixty two volunteers, with the approval of their wives, were recruited. Thirty two were submitted to surgical procedure and thirty participated as a control group. A couple of months after surgery the increase in length had been around 2.0-2.5 cm. The lengthening surgical procedure was not described, but it can be assumed that a couple of ligaments were cut.

Before starting the experiment the wives were asked to give their opinion about the size of their husbands' penises: 87% said they did not understand why their husbands decided to enlarge their penis when its size seemed adequate for its purpose. The same question was asked after the experiment, and this time, 67% of women had changed their opinion. Now, the women attributed superior quality of sexual intercourse to the larger penis, incomparable to the previous performance. They claimed that now they were able to reach a level of pleasure never imagined. Going from −87% to +67% is an impressive statistical change.

The Kinsey study which is one of the biggest and most famous penis size studies ever done was performed in 1948 and involved 3,500 college males. In Kinsey's study the average flaccid length was found to be 3.89 inches, flaccid girth 3.75 inches and in average erect length was 6.21 inches, the average erect girth was 4.85 inches.

Three major structures compose in the human penis: the urethra and two long cylinders, the erectile bodies. The urethra with a thick, spongy cylinder around it is for conducting urine and ends at the glans of the penis. The skin on the glans is very sensitive and is normally protected by the foreskin, which acts as a cover. The erectile bodies, long cylinders that is located next to each other at the back of the penis. They contain blood. During erection, the amount of blood inside the cylinders increases. While inflow increases, the outflow of the blood decreases and the cylinders are filled to the limit with blood and will stand upright, causing erection of the penis. To ensure a good blood supply, several blood vessels run towards erectile bodies and the dense web of small nerve fibers ensure the opening and closing of the vessels during erection.

Since there are no stiff structures like bones in human penis (in some animals the penis equipped with a small bone) in the penis to give it rigidity, the penis is connected to the pubic bone by strong connective tissue that tend to cause the penis during erection to point slightly upwards.

Suspensory and Fundiform Ligaments

The suspensory and fundiform ligaments are an "evolution leftover" that has no importance at all in the modem man's body. On men and monkeys, the support and the orientation of the erection is controlled by hydraulic pressure. In the other animals, the erection support is mechanical. In some animals for the penis to achieve an erection, there is a muscular device that project the penis forward and another muscular device that retract the penis after sexual intercourse. The suspensory and fundiform ligaments would be this muscle. In the men this is totally unnecessary. This structure consists of fiber-elastic tissue that in some men is very developed and is constantly retracting the member, but never supporting or orienting it. The visual part of the penis is only the external part. The rest of the penis is inserted seven to ten centimeters into the male's pubic region. This internal part is anatomically known as the crus of penis (crus corporis cavernosi penis). It connects to the pubic bone through the fundiform and suspensory ligaments that curves the member downward. When these ligaments were separated by cutting, the part of the penis previously attached to the pubic bone is externalized, increasing penile length by a few centimeters. For some men the removal of the extra pubic fat can add a few extra centimeters as well.

Penile lengthening surgery

Increasing penile length requires releasing the suspensory and fundiform ligaments and wearing weights after surgery (stretching physiotherapy exercises). The desirable success in lengthening procedure directly depends upon on two equal components: ligament detachment and physiotherapy. The body of the penis is anchored to the pubic bone, and a thickening of the rectus muscle anchors the top (i.e. the base) of the penis. The rectus muscles, or "abs," are the muscles in the middle of the abdominal wall. This thickened layer, called the fundiform ligament, extends off the rectus muscle to anchor the penis. When this ligament is cut, in addition to suspensory ligament as in so-called penis-lengthening operations, the penis may appear longer although it simply hangs lower from the body because it has been disconnected. Releasing the ligament partially frees the penis from its pubic bone attachments, dropping it to a lower position, which may increase the portion of the penile length outside the body.

Prior Art Techniques for Penal Enlargement

There are two popular techniques for penal enlargement. The first involves transplanting the patients own skin along with attached fat from another part of his body to his penis. An example is described in US Patent Application, Pub. No. 2006/0157066. The second known technique involves inserting treated donated skin under portions of the patient's penile skin. In this second technique an incision is made in the penile skin at the base of the skin adjacent to the pubic region and another incision is made in the skin just behind the glans of the penis. Sections of the treated donated skin are inserted under the patient's penile skin along the top side of the penis. These sections are stitched to the patient's skin at the base of the skin and at the incision just behind the glans of the penis. This donated skin is available from LifeCell Corporation with offices in Branchburg, N.J. and is sold under the trade name AlloDerm. This material is also known a free dermal matrix graft. This donated skin is FDA approved to use for skin replacement for bum victims in the US. It is sold in a frozen state and when thawed in warm saline water is soft and flexible. It can be stretched about 20 percent as compared to penile skin which can be stretched about 50 percent or more.

The following papers provide some description of phalloplasty prior art:

Harold Reed: Augmentation phalloplasty with Girth Enhancement Employing Autologous Fat Transplantation: A Preliminary Report. The American Journal of Cosmetic Surgery. 1994; 11, 2, 85-90.

Alexander Krakovsky: State of the Art in Phalloplasty. The American Journal of Cosmetic Surgery. 2005; 22, 3, 172-178.

What is needed is a better technique for penile enlargement.

SUMMARY OF THE INVENTION

The present invention provides a technique for penile enlargement. The apparent length of the penis is first increased by cutting ligaments that attach the penis to the pubic bone. Then the girth of the penis is increased by making two cuts making two apertures in the penile skin near the base of the penis and near the glans of the penis and inverting the skin from the top side of the penis so that the glans of the penis protrudes through one of the skin aperture substantially all of the exposed penis protrudes through the other skin aperture, leaving at least the top half of the penis skinless defining a bare penile region. One or more layers of donated skin is attached to the patient's skin covering the bare region. Then the patients skin from the back of his penis is re-inverted approximately back to its original position and covering the donated skin stitched to the patient's fascia that covers both cavernous bodies (Buck's fascia). The two incisions are then closed.

Extra Length

In preferred embodiments a few centimeters of extra length is added to the penis by cutting ligaments and using techniques already know in the prior art, details of which are described below.

Additional Girth

Additional girth is provided with a special technique invented by Applicant. An incision is made in the penile skin across the base of the penis on the top side from about 4 o'clock to about 8 o'clock (straight up being 12 o'clock). Another incision is made in the penile skin on the top side of the penis about ⅛ inch from the glans of the penis also from 4 o'clock to 8 o'clock. The top ¾ portion patient's penile skin is the pulled over the glans of the penis leaving the top ⅔ of the patient's penile skin inside out along the bottom of the patient's penis. The patient's skin on the bottom ¼ of his penis is generally undisturbed while the top ¾ of the penis is without skin.

(If this is difficult for you, the reader, to visualize he should put on a long loose tee-shirt. Tuck the bottom front ¼ of the tee-shirt in your pants [or pen the bottom of the front of the tee shirt to your pants. Then grip the front of the tee-shirt its neck in your teeth. Now while keeping the bottom front of your tee-shirt tucked in, or attached to, your pants and the neck of the tee shirt clenched in your teeth, pull the back of the tee-shirt over your head. You will notice that your back is bare and the tee-shirt is hanging in front of you clinched at the neck in your teeth attached at the bottom to your pants.)

Just as you back is made bare with the tee shirt procedure described above, the penis skin inversion procedure makes bare of skin the top ¾ of the penis. One, two, three or more layers of donated skin is attached to the penis by stitching the donated skin to the patients penile fascia (Buck's fascia) along both sides, at the base and near the glans of the penis where the incisions were made. After the donated skin has been attached the patient's own skin is pulled back over the glans of his penis to its original position covering up the stitched on donated skin. The two incisions are then close by stitching.

Enlargement of the Glans of the Penis

In preferred embodiments the glans of the penis is enlarged with a technique invented by Applicant. With the skin removed from the top ¾ of the penis as described above, two caverns about 5 mm in diameter and about two cm long are opened in the spongy tissue of the glans. These caverns are stuffed with rolled up donated skin tissue and stitched in place.

Erectile Dysfunction

A combination technique is described for men who are bothered with erectile dysfunction and a concern that their penises are too small.

BRIEF DESCRIPTION OF THE DRAWINGS

FIGS. 4A and 4B show two views of the penis ready for attachment of donated skin.

FIGS. 4C and 4D show donated skin attached on the top side of the penis.

DETAILED DESCRIPTION OF PREFERRED EMBODIMENTS

Figure 1:
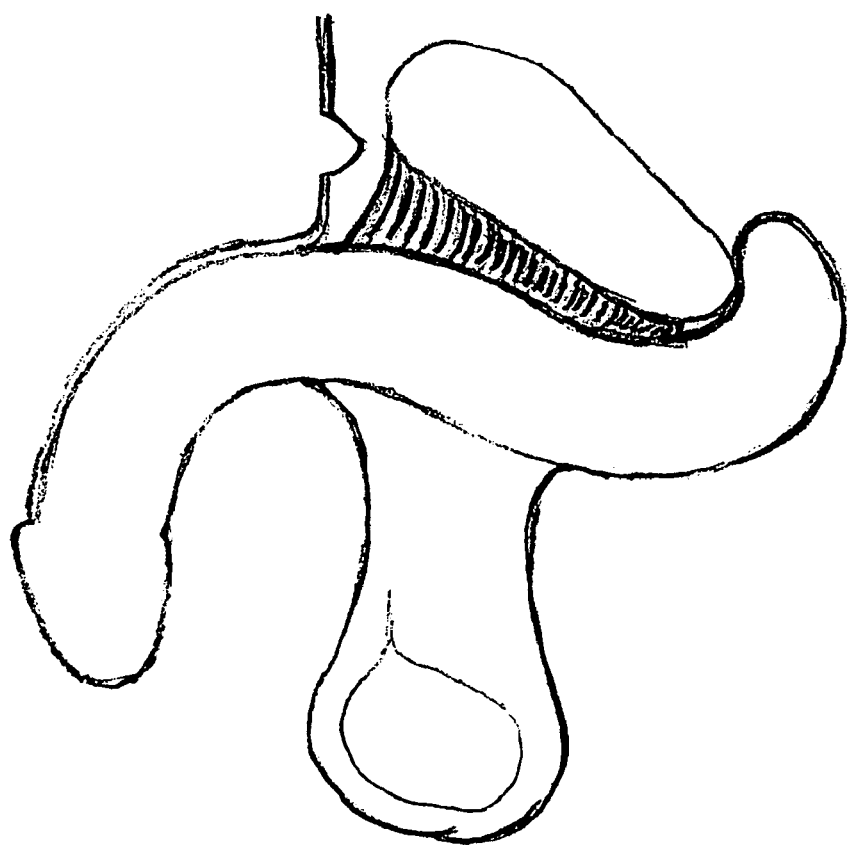
FIG. 1 is a sketch showing the penis attached with multiple ligaments to the pubic bone and an incision made to begin penal lengthening.
Figure 2:
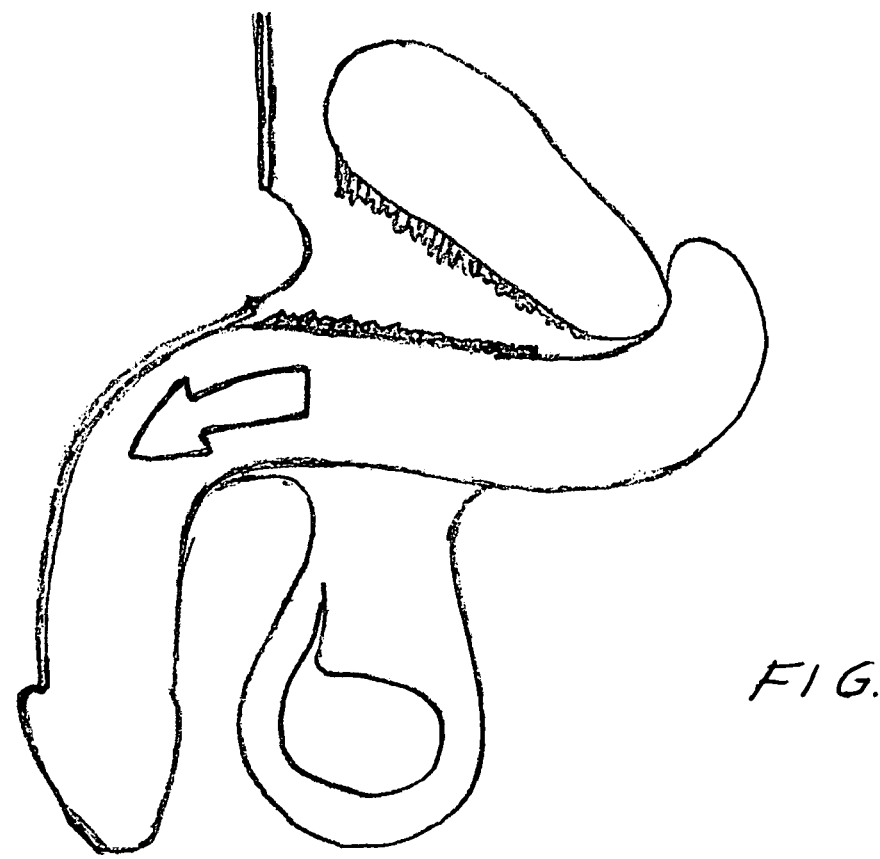
FIG. 2 is a sketch showing the ligaments cut to provide penile lengthening.
Figure 3:
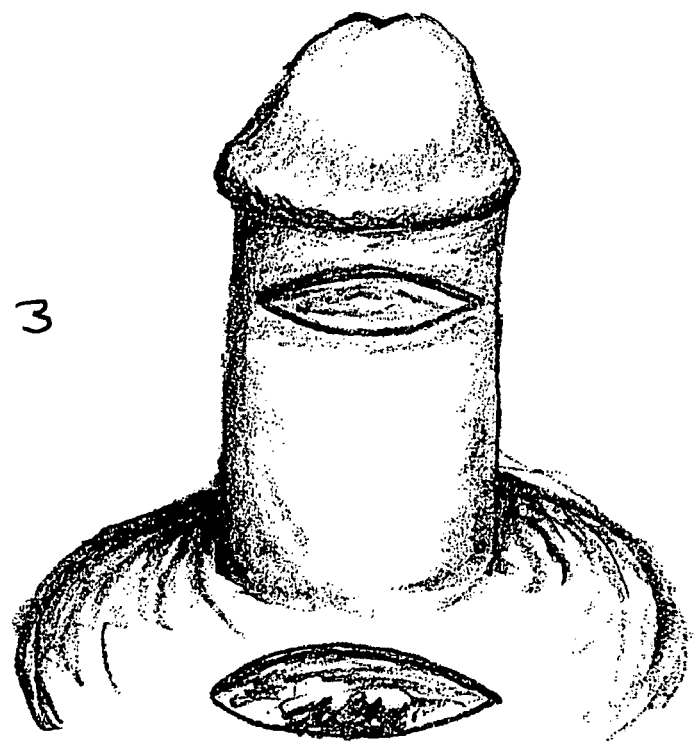
FIG. 3 is a sketch of a penis with two incisions made in preparation for pulling the skin from the top side of the penis over the glans of the penis.

Preferred embodiments of the present invention can be described by reference to the drawings. These descriptions describe processes for increasing the length and girth of the human penis.

Preparation

The patient should be previously anesthetized, with the application of standard monitoring by American Society of Anesthesiology, which includes EKG, blood pressure, pulse monitor and quantity of oxygen by pulse oximeter. The patient should be put in the supine position on the operating table and the patient's genitalia should be prepped and draped in sterile fashion. Local anesthesia including penile block should be applied.

Lengthening Procedure

Lengthening procedure is performed today through curvilinear incision in the infrapubic region at the base of the penis that approximately 5 cm in length. Extreme care is taking to avoid contact with any significant blood vessels and nerves. With a very steep Trendelenburg position suspensory and fundiform ligaments are usually easy to identify. Anatomical structure of fundiform and suspensory ligaments in the vast majority of the patients are on the level of very well developed. Traction has to be applied to the penis to better identify the ligaments from the pubis bone to the shaft of the penis. In order to completely free up the penis from the attachment to the pubic bone, both ligaments have to be cut in full. The suspensory ligament positioned very deep and sometimes is difficult to reach the tip of it. Some surgeons are satisfied with partial detachment of the ligaments from the pubic bone. With incomplete separation, the desirable surgical result is not always achievable. In some patients the depth of the wound could be up to 12-15 cm from the skin. In these cases extreme care has to be undertaken to avoid major blood vessels and nerves. With complete separation of the penis from pubic bone the portion of the penis that becomes available in average is no more then ¾-1 inch.

In the floor of this wound there are several collateral ligaments that (to the best of Applicant's knowledge) have never been described before in medical literature. Lack of the description of these collateral ligaments was related to inadequate observation of the floor of the wound during lengthening procedure in the past. In other words, all previous descriptions of the penile lengthening procedure represented inadequate depth and incomplete detachment of the penis from the pubic bone. Complete lengthening surgery includes incise of fundiform, suspensory and multiple lateral ligaments to completely separate penis from the pubic bone.

The surgeon can only free up the portion of the penis that attached to the pubic bone. This quantity has individual variation and the surgeon should never promise how much post surgical gain the patient might achieve. The final result of the lengthening procedure equally depends upon the complete separation of the penis from the pubis bone and adequate post surgical stretching exercise therapy (physiotherapy) performed by the patient.

The wound has to be closed layerly. Additional rejuvenation of penile pubic junctions and scrotal pubic junctions has to be undertaken emphasizing the angle of the penis and pubic area. This rejuvenation could be achieved by changing sagging angle that appears when man aging.

Girth Enhancement Surgery with Free Dermal Matrix Graft (FDMG)

Historically as explained in the background section, surgeons have used Dermal Graft which is patient's own skin that is taken by the surgeon and placed on the penis to increase the penis girth. This procedure usually leaves the patient with a huge scar on they body which is very undesirable. Free Dermal Matrix Graft (FDMG) is the most up to date surgical technique for penile augmentation. Penile cosmetic augmentation surgery with FDMG is supra cavernosum phalloplasty surgery that performs in flaccid state only. FDMG acellular tissue regeneration matrix is processed from donated human skin. The allograft skin is minimally processed to remove epidermal and dermal cell while preserving the remaining bioactive components and structure of dermis. The resulting allograft serves as a framework to support cellular repopulation and vascularization.

The details of the surgery designed to increase the girth of the penis is now described.

The patient should be previously anesthetized, with the application of standard monitoring by American Society of Anesthesiology, which includes EKG, blood pressure, pulse monitor and oxygen monitoring by pulse oximeter. The patient should be put in the supine position on the operating table and the patient's genitalia should be prepped and draped in sterile fashion. Local anesthesia including penile block should be applied. Prior to initiation of the surgery, FDMG should be prepared according to patient anatomy.

For different purpose and anatomical sizes, two, three, four or more sheets of 4×7 cm extra-thick FDMG should utilized. If there is different FDMG dimension available, they could be used as well and trimmed according to the patient anatomy. Before surgery FDMG has to be placed in normal saline solution to become softer and ready to be stitched. The FDMG should be oriented so that all pieces were uniform positioned. Two, three, four or more FDMG sheets should be stitched together to match the patient's anatomy. FDMG is then altered and trimmed in a meticulous manner so that it could easily be incorporated along the shaft of the penis as well as into the infrapubic region in the proximal portion of the penis. Any other pieces of FDMG might be used to enlarge the shaft of the penis. (Alternatively when other than FDMG tissue becomes available including patient's own tissue grow, regeneration or repopulation using biological engineering technology, they can be used for that purpose.)

The procedure should be started with a curvilinear incision in the infrapubic region at the base of the penis approximately 5 cm in length. The subcutaneous tissue must be incised and dissected utilizing needle-tip cautery, as well as a blunt dissection. At this point, a tonsil clamp should be inserted down through the incision to the region of the pubic bone. The tonsil clamp should then be opened and the tissue must be spread so that a pocket could be developed in the infrapubic region. Then an incision should be made approximately 5 mm proximal to the glans of the penis. Needle tip cautery must be utilized to incise and dissect down through the dartos fascia to Buck's fascia. Once again, hemostasis should be maintained utilizing the Bowie. Nerves and large blood vessels must be avoided. This was a single incision along the dorsal aspect of the proximal portion of the glans from 8 o'clock-to 12 o'clock-to 4 o'clock.

At this point, attention has to be directed to the shaft of the penis. Utilizing the scissors, a one large pocket should be developed along Buck's fascia underneath the dartos fascia, along the dorsal aspect of the corpora cavernosum all the way down to the base of the penis into the pubic region. This large pocket has therefore been created from also from 8 o'clock-to 12 o'clock-to 4 o'clock along the dorsum of the penis into the pubic region. Hemostasis should be maintained utilizing the Bowie. Careful dissection must been accomplished all the time. Once the pocket along the shaft of the penis become adequate and the corpora cavernosum was completely free, the skin on the top side of the penis has to be inverted. The corpora covered by Buck's fascia has to be completely freed up from the surrounding tissue in order to incorporate FDMG. Then FDMG in the corpora region of the penis should then be tacked down utilizing absorbable interrupted sutures through the dorsal and lateral aspect of Buck's fascia on both sides.

At this time, care should be directed to make sure that FDMG was seated in an appropriate position, lying down nicely and symmetrically on both sides in absolutely uniform fashion. After that, the penis skin from the top side of the penis should be inverted backward into its original position covering the FDGM. Then, the distal penile incision should be closed. The initial layer was the deep dartos layer of the distal penis incision and then the skin layer should be closed utilizing absorbable simple running and vertical mattress running sutures.

The proximal portion of FDMG graft should be secured to the proximal portion of Buck's fascia of corpora cavernosum. It has to be accomplished by utilizing absorbable sutures that should be placed superficially in the pubic region and throughout FDMG.

Careful inspection of the penis should then be done to make sure that FDMG is fitting appropriately and its appropriate orientation was undertaken and that the FDMG is in good position, sitting flat, with lateral aspects flat as well and no twisting. If there is no restriction of FDMG on the corpora, the penis should be easily advanced forward and stretched. The infrapubic wound should be inspected for bleeding and hemostasis should be obtained utilizing cautery. Once hemostasis has been obtained, the pubic wound should be irrigated multiple times with antibiotic solution.

Additional rejuvenation of penile pubic junctions and scrotal pubic junctions should be undertaken emphasizing the angle of the penis and pubic area. This rejuvenation could be achieved by changing the sagging angle that appears when man ages.

Glanular Enhancement Surgery with Free Dermal Matrix Graft

The details of the surgery designed to increase the glans of the penis is now described.

There are two version of these procedures are going to be described. Glanular enhancement procedure is a technique that might compliment lengthening and girth enhancement and/or might be performed independently.

Figure 4:
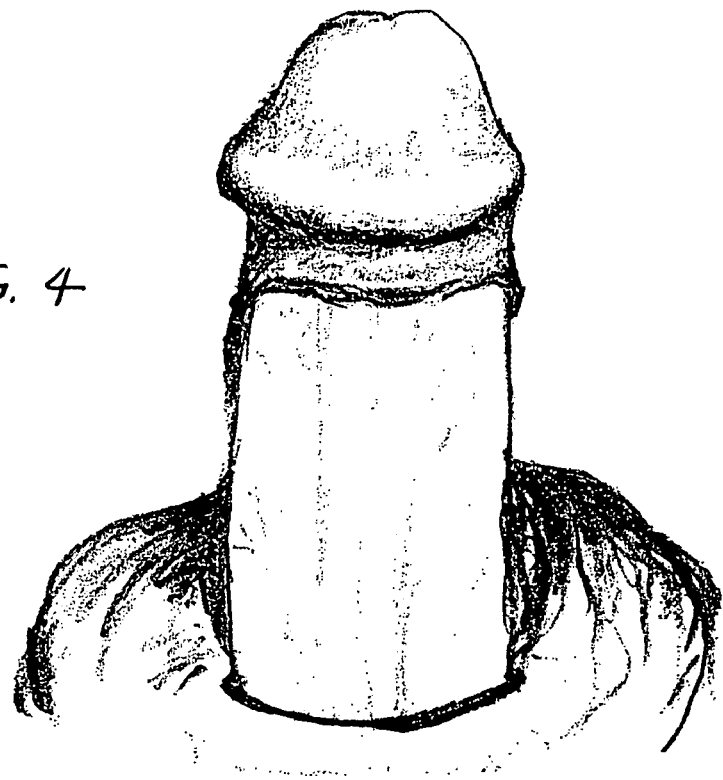
FIG. 4 is a sketch showing the penis with the skin from the tops side of the penis inside out and flipped over the glans of the penis.

First version of glanular enhancement surgery is a standard enhancement and the second version is a maximum enhancement. This procedure should be applied after the skin has been inverted off the top portion of the penis as shown in FIG. 4 but before the donated skin has been added for girth enhancement. Utilizing tenotomy scissors, pockets should be developed underneath the glans on both the right and left sides of the glans from 1 to 2 cm in length. Rolled up FDMG then should be checked to make sure that it fits appropriately in the pockets and underneath the glans.

Figure 5:
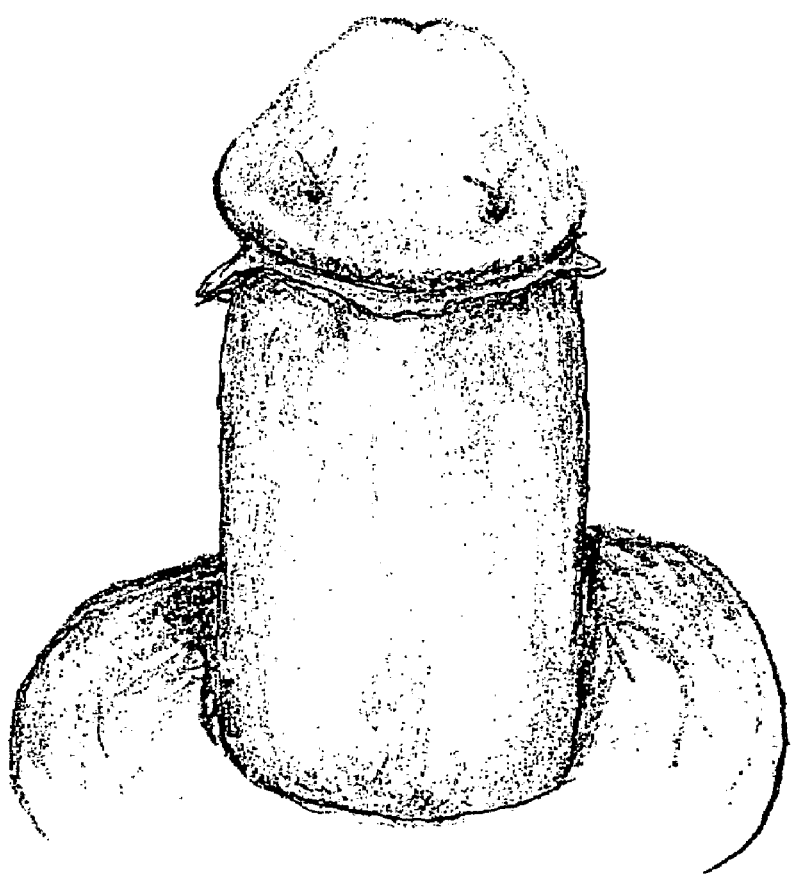
FIG. 5 shows where rolled up dermal skin has been stitched to the skin of the glans of the penis.

The distal arms of FDMG should be sutured underneath the glans utilizing pull-through technique with straight needle and dissolvable interrupted sutures. Each arm of FDMG then has to be placed into the appropriate pocket underneath the glans on both right and left sides. Care must be undertaken to make sure that FDMG fit well into the pockets. The two FDMG arms then should be secured to the glans of the penis with stitches as shown in FIG. 5.

For additional enlargement of the glans two more pockets should be prepared in the middle of the glans of the penis. Additional pieces of FDMG should be rolled and stitched as described above. Using additional curved surgical instrument, the FDMG should be inserted in one pocket, going through the midline of the glans of the penis and come out from the other pocket, making an inverted U shape inside the glans of the penis. The middle portion of FDMG should stay inside the glans. Any protruding amount of FDMG should be trimmed and both pockets should be closed with interrupted absorbable sutures.

Correction of Erectile Dysfunction

In some cases a man desiring a larger penis also suffers from erectile dysfunction. Applicant and another has invented and patented at procedure for correction of erectile dysfunction. That patent is U.S. Pat. No. 5,454,840 that is incorporated herein by reference. The technique involves stimulation of nerves in the pubic region including nerves in the penis. The technique includes an implanted device called a "Potency Package" and electrodes connected to nerves in the pubic region. In preferred embodiments of the present invention the teachings of this application are combined with the teaching of U.S. Pat. No. 5,454,840. Preferably the surgery to enlarge the penis is performed at the same time as the surgery for implanting the stimulation device and electrodes.

While the present invention has been described in terms of preferred embodiment, persons skilled in this art will understand that many changes, additions and modifications could be made without deviating from the basic concepts of the present invention. For example various types of medically approved stitching techniques could be used. Penile girth can be provided in a variety of sizes determined by the number of layers of donated skin used; also by the choice of the thickness of each of the skin layers. Therefore, the scope of the present invention should be determined by the claims and their legal equivalents.

What is claimed is:

1. A process for human penile enlargement comprises the steps of:
    A) increasing the apparent length of the penis by cutting ligaments that attach the penis to the pubic bone,
    B) increasing the girth of the penis via the following steps:
       1) making a first incision about 3 to 6 cm long through the skin of the penis (defining a first skin aperture) at a first incision location across the base of the penis from about 4 o'clock to about 8 o'clock assuming the circumference of the penis is measured by clock numbers with 12 o'clock being straight up;
       2) making a second incision across the penis through the skin of the penis (defining a second skin aperture) at a second incision location about 0.5 cm from the base of the glans of the penis from about 4 o'clock to about 8 o'clock;
       3) inverting the skin from the top side of the penis so that the glans of the penis protrudes through the second skin aperture substantially all of the exposed penis protrudes through the first skin aperture, leaving at least the top half of the penis skinless defining a bare penile region bordered by the first incision location, the second incision location and two folded penile skin location along the sides of the penis between the first incision location and the second incision location;

4) attaching one or more layers of donated skin to the patients penile skin with a medically approved stitching technique at the first location at the base of the penis, at the second location near the glans of the penis and at the penis and at the two folded penile skin locations;

5) re-inverting the skin from the top side of the penis approximately back to its original position and covering the donated skin stitched to the patient's skin;

6) closing the first and second incisions using a medically approved stitching technique.

2. The process as in claim 1 and further comprising glans enlarging steps of enlarging the glans of the penis wherein said glans enlarging steps include creating two cavities along two sides of the glans of the penis in the spungy region of the glans of the penis and filling these cavities with rolled donated skin.

3. The process as in claim 2 and further comprising steps of creating a U-shape region near the center of the glans of the penis and filling the U-shaped region with rolled-up donated tissue.

4. The process as in claim 1 wherein the medically approved stitching techniques include stitching with absorbable stitches.

5. The process as in claim 1 wherein the medically approved stitching techniques include stitching with medical staples.

6. The process as in claim 1 wherein said one or more layers is two layers.

7. The process as in claim 1 wherein said one or more layers is three layers.

8. The process as in claim 1 wherein said one or more layers is four layers.

9. The process as in claim 1 wherein said one or more layers is five layers.

* * * * *